US010226434B2

(12) United States Patent
Radtke et al.

(10) Patent No.: US 10,226,434 B2
(45) Date of Patent: Mar. 12, 2019

(54) DESIGN, SYNTHESIS AND METHODS OF USE OF ACYCLIC FLEXIMER NUCLEOSIDE ANALOGUES HAVING ANTI-CORONAVIRUS ACTIVITY

(71) Applicant: UNIVERSITY OF MARYLAND, BALTIMORE COUNTY, Baltimore, MD (US)

(72) Inventors: Katherine L. Radtke, Baltimore, MD (US); Hannah Peters, Baltimore, MD (US); Johan Neyts, Leuven (BE); Dirk Jochmans, Leuven (BE); Eric J. Snijder, RC Leiden (NL)

(73) Assignees: University of Maryland, Baltimore County, Baltimore, MD (US); Katholieke Universiteit Leuven/Lieden University Medical Center, RC Leiden, Belgium (NL)

( * ) Notice: Subject to any disclaimer, the term of this patent is extended or adjusted under 35 U.S.C. 154(b) by 0 days.

(21) Appl. No.: 16/025,284

(22) Filed: Jul. 2, 2018

(65) Prior Publication Data

US 2018/0303768 A1 Oct. 25, 2018

Related U.S. Application Data

(63) Continuation of application No. 15/546,818, filed as application No. PCT/US2016/015327 on Jan. 28, 2016, now Pat. No. 10,058,516.

(60) Provisional application No. 62/109,667, filed on Jan. 30, 2015, provisional application No. 62/195,968, filed on Jul. 23, 2015.

(51) Int. Cl.

| | |
|---|---|
| ***C07D 403/04*** | (2006.01) |
| ***A61K 31/08*** | (2006.01) |
| ***A61K 31/506*** | (2006.01) |
| ***A61K 45/06*** | (2006.01) |
| ***A61K 31/4178*** | (2006.01) |

(52) U.S. Cl.

CPC .......... *A61K 31/08* (2013.01); *A61K 31/4178* (2013.01); *A61K 31/506* (2013.01); *A61K 45/06* (2013.01); *C07D 403/04* (2013.01); *A61K 2300/00* (2013.01); *Y02P 20/582* (2015.11)

(58) Field of Classification Search

CPC .................................................... C07D 403/04

See application file for complete search history.

(56) References Cited

U.S. PATENT DOCUMENTS

2007/0060535 A1 3/2007 Adamson et al.

FOREIGN PATENT DOCUMENTS

WO WO2005020884 3/2005
WO WO2005020885 3/2005

OTHER PUBLICATIONS

Chemical Abstracts Registry No. 550-33-4, Nov. 16, 1984.
Chemical Abstracts Registry No. 19186-33-5, Nov. 16, 1984.
In Global alert and response. Middle East Respiratory syndrome coronavirus (MERS-CoV); World Health Organization: 2015; vol. 2014.
In Zovirax Prescribing Information; U.S. Food and Drug Administration: 2003; NDA 18-603/5-027.
Al-Hazmi, A. Challenges presented by MERS corona virus, and SARS corona virus to global health, *Saudi Journal of Biological Sciences*, 23 (2016), pp. 507-511.
Al-Tawfiq, J.A. et al. Ribavirin and interferon therapy in patients infected with the Middle East respiratory syndrome coronavirus: an observational study, *Int. J. Infect. Dis.*, 20 (2014), pp. 42-46.
Boncel, A. et al. Novel 5-(N-Alkylaminouracil) Acyclic Nucleosides, *Synthesis-Stuttgart* (2011), pp. 603-610.
Chen, F. et al. In vitro susceptibility of 10 clinical isolates of SARS coronavirus to selected antiviral compounds, *J. Clin. Virol.*, 31 (2004), pp. 69-75.
De Wilde, A.H. et al. MERS-coronavirus replication induces severe in vitro cytopathology and is strongly inhibited by cyclosporin A or interferon-alpha treatment, *J. Gen. Virol.*, 94 (2013), pp. 1749-1760.
De Wilde, A.H. et al. Screening of an FDA-Approved Compound Library Identifies Four Small-Molecule Inhibitors of Middle East Respiratory Syndrome Coronavirus Replication in Cell Culture, *Antimicrob. Agents Chemother*, 58 (2014), pp. 4875-4884.
Falzarano, D. et al. Treatment with interferon-alpha 2b and ribavirin improves outcome in MERS-CoV-infected rhesus macaques *Nat. Med.*, 19 (2013), pp. 1313-1317.
Fehr, A.R. et al. Coronaviruses: An Overview of Their Replication and Pathogensis, *Methods Mol. Biol.* 1282 (2015) pp. 1-23.
Fouchier, R. A. et al. A previously undescribed coronavirus associated with respiratory disease in humans. *Proc Natl Acad Sci U S A* 101 (2004), pp. 6212-6216.
Furman, P.A. et al. Acyclovir Triphosphate is a Suicide Inactivator of the Herpes-Simplex Virus DNA Polymerase, *J. Biol. Chem.*, 259 (1984), pp. 9575-9579.
Grant, R. et al. Grant & Hackh's Chemical Dictionary, 1987 ($5^{th}$ ed.) New York, NY; McGraw-Hill, p. 313.
Jochmans, D. et al. A novel method for high-throughput screening to quantify antiviral activity against viruses that induce limited CPE. *J Virol Methods* 183 (2012), pp. 176-179.

(Continued)

*Primary Examiner* — Laura L Stockton

(74) *Attorney, Agent, or Firm* — Marianne Fuierer; Olive Law Group, PLLC

(57) ABSTRACT

The present invention is directed to compounds, methods and compositions for treating or preventing viral infections using nucleosides analogs. Specifically, the present invention provides for the design and synthesis of acyclic fleximer nucleoside analogues having increased flexibility and ability to alter their conformation structures to provide increased antiviral activity potential with the result of inhibiting several coronaviruses.

12 Claims, No Drawings

(56) References Cited

OTHER PUBLICATIONS

Kuiken, T. et al. Experimental human metapneumovirus infection of cynomolgus macaques (*Macaca fascicularis*) results in virus replication in ciliated epithelial cells and pneumocytes with associated lesions throughout the respiratory tract. *Am J Pathol*, 164 (2004), pp. 1893-1900.
McGuigan, C. et al. Design, synthesis and evaluation of a novel double pro-drug: INX-08189. A new clinical candidate for hepatitis C virus *Bioorg. Med. Chem. Lett.*, 20 (2010), pp. 4850-4854.
McGuirt, P.V. et al. Acyclovir Inhibition of Viral DNA Chain Elongation in Herpes Simplex Virus-Infected Cells, *Am. J. Med.*, 73 (1982), pp. 67-71.
Mee, S.P. et al. Significant enhancement of the Stille reaction with a new combination of reagents-copper(I) iodide with cesium fluoride, *Chem. Eur. J.*, 11 (2005), pp. 3294-3308.
Momattin, H. et al. Therapeutic Options for Middle East Respiratory Syndrome Coronavirus (MERS-CoV)—possible lessons from a systematic review of SARS-CoV therapy, *Int. J. Infect. Dis.*, 17 (2013), pp. e792-e798.
Morgenstern, B. et al. Ribavirin and interferon-beta synergistically inhibit SARS-associated coronavirus replication in animal and human cell lines, *Biochem. Biophys. Res. Commun.*, 326 (2005), pp. 905-908.
Niedzwicki, J.G. et al. Structure-Activity Relationship of Ligands of Human Plasma Adenosine Deaminase$_2$, *Biochemical Pharmacology*, 41 (1991) pp. 1615-1624.
Peiris, J.S.M. et al. Coronavirus as a possible cause of severe acute respiratory syndrome, *Lancet*, 361 (2003), pp. 1319-1325.
Peters, H.L. Design, synthesis and evaluation of a series of acyclic fleximer nucleoside analogues with anti-coronaviurs activity, *Bioorganic & Medical Chemistry Letters*, 25 (2015) pp. 2923-2926.
Pyrc, K. et al. Identification of new human coronaviruses, *Expert Rev. Anti-infect. Ther.*, 5 (2007), pp. 245-253.
Quirk, S. et al. Substrate discrimination by the human GTP fucose pyrophosphorylase, *Biochemistry*, 44 (2005), pp. 10854-10863.
Quirk, S. et al. Identification of catalytic amino acids in the human GTP fucose pyrophosphorylase active site, *Biochemistry*, 44 (2005), pp. 13172-13178.
Salim, S. Molecular chameleons: design and synthesis of a second series of flexible nucleosides, *Doctoral dissertation, Georgia Institute of Technology*, 2004, pp. 1-149.
Schinazi, R. Synthesis of 5-(Dihydroxyboryl)-2' deoxyuridine and Related Boron-Containing Pyrimidines, *J. Org. Chem.*, 50 (1985), pp. 841-847.
Seley, K.L. et al. "Fleximers". Design and Synthesis of Two Novel Split Nucleosides, *Org. Lett.*, 3 (2001), p. 3209-3210.
Seley, K.L. et al. "Fleximers". Design and Synthesis of a New Class of Novel Shape-Modified Nucleosies, *Org. Chem.*, 67 (2002), p. 3365.
Seley, K. L. et al. Unexpected inhibition of S-adenosyl-L-homocysteine hydrolase by a guanosine nucleoside, *Bioorg. Med. Chem. Lett.*, 13, (2003) pp. 1985-1988.
Seley, K. L. et al. "Molecular chameleons". Design and synthesis of C-4-substituted imidazole fleximers, *Org. Lett.*, 7 (2005), pp. 63-66.
Smith, E.C. et al. Coronavirus Lacking Exoribonuclease Activity Are Susceptible to Lethal Mutagenesis: Evidence for Proofreading and Potential Therapeutics, *PLoS Pathog.*, 9 (2013), p. e1003565, 1-11.
Tan, E.L. et al. Inhibition of SARS Coronavirus Infection in Vitro with Clinically Approved Antiviral Drugs, *Emerg. Infect. Dis.*, 10 (2004), pp. 581-586.
Vanpouille, C. et al. A new class of dual-targeted antivirals: monophosphorylated acyclovir prodrug derivatives suppress both human immunodeficiency virus type 1 and herpes simplex virus type 2, *J. Infect. Dis.*, 201 (2010), pp. 635-643.
Wauchope, O.R. et al. Synthetic Routes to a Series of Proximal and Distal 2'-Deoxy Fleximers, *Synthesis*, 44 (2012), pp. 3496-3504.

DESIGN, SYNTHESIS AND METHODS OF USE OF ACYCLIC FLEXIMER NUCLEOSIDE ANALOGUES HAVING ANTI-CORONAVIRUS ACTIVITY

CROSS-REFERENCE TO RELATED APPLICATIONS

This application is a continuation of U.S. patent application Ser. No. 15/546,818, filed on Jul. 27, 2017, Now U.S. Pat. No. 10/058,516 which was filed under the provisions of 35 U.S.C. § 371 and claims the priority of International Patent Application No. PCT/US2016/015327 filed on Jan. 28, 2016 which in turn claims priority to U.S. Provisional Application No.: 62/109,667 filed on Jan. 30, 2015 and U.S. Provisional Application No.: 62/195,968 filed on Jul. 23, 2015, the contents of both are incorporated by reference herein for all purposes.

STATEMENT OF FEDERALLY SPONSORED RESEARCH

This invention was made with government support under Grant Number R21AI097685 and T32GM066706 awarded by the National Institutes of Health. The government has certain rights in the invention.

FIELD OF INVENTION

The present invention is directed to compounds, methods and compositions for treating or preventing viral infections using nucleosides analogues. Specifically, the present invention provides for the design and synthesis of acyclic fleximer nucleoside analogues having increased flexibility and ability to alter their conformation to provide increased antiviral activity potential with the result of inhibiting several coronaviruses.

BACKGROUND OF THE INVENTION

Nucleoside analogues as a class have a well-established regulatory history, with many currently approved by the US Food and Drug Administration (US FDA) for treating viruses and cancer, including but not limited to leukemias, lymphoms, cervical cancer, skin cancers, human immunodeficiency virus (HIV), hepatitis B virus (HBV), hepatitis C virus (HCV), herpes simplex, varicella zoster virus (VZV) and respiratory syncytial virus (RSV), among others. However, there is a current challenge in developing cancer and antiviral therapies to inhibit cancer cells or viral replication without injuring the host cell.

Currently there are no approved treatments or vaccines for human coronaviruses (HCoVs) or potentially lethal zoonotic coronaviruses (CoVs), such as severe acute respiratory syndrome (SARS) or Middle East respiratory syndrome (MERS). HCoVs were first identified in the 1960s with only two species known at the time, HCoV-229E and HCoV-OC43. These viruses are known to cause a large number of common colds with typically mild symptoms, with the exception of those suffering from other illnesses, particularly immunocompromised systems. (9) In 2002 a new coronavirus pathogen associated with severe lung disease emerged in Guangzhou, and later spread to Southern China and Hong Kong. The new virus was named SARS-CoV, (10) and before the end of the outbreak over 8,000 cases were confirmed in several countries and with almost 8,000 fatalities. Since then two additional coronaviruses, HCoV-NL63 and HCoV-HKU1, were discovered in humans and most recently, in 2012, MERS-CoV was identified as a second zoonotic coronavirus that can cause lethal respiratory infections in humans.

The current MERS outbreak has been ongoing for almost three years, with well over a thousand confirmed cases having been documented, with a mortality rate of about 40%. (1) Since the 2002-2003 SARS outbreaks, there have been extensive efforts to target the coronavirus family, including the screening of libraries of already approved antiviral drugs such as acyclovir (ACV), ganciclovir, lamivudine, and zidovudine. Unfortunately, none of these well-known antiviral drugs exhibited any activity against SARS-CoV or MERS-CoV in vitro. (2)

The SARS-CoV screening efforts did, however, yield a small number of leads including the nucleoside analogue ribavirin, a guanosine-like analogue that has exhibited broad-spectrum antiviral activity. (2-7) Ribavirin was found to inhibit coronavirus replication in vitro, but with an inhibitory concentration much higher (500-5000 μg/ml) than that needed to inhibit other viruses (50-100 μg/ml). Consequently, it does not appear to represent a viable treatment option. Moreover, a recent study has suggested that in the case of the coronaviruses, ribavirin's antiviral activity is not primarily due to lethal mutagenesis, but rather to its effect on the cell's Guanosine-5'-triphosphate (GTP) biosynthesis. (8) Beyond these studies, there are few reports of nucleoside inhibitors being studied or developed to combat coronavirus infection.

The need for new and more effective antiviral therapeutics, particularly those targeting emerging and reemerging infectious diseases and pathogens continues to increase. Thus, in light of the above discussion, there is a need for discovering and providing new and more efficient antiviral drugs.

SUMMARY OF THE INVENTION

The present invention provides for flexible and modified nucleoside analogues that allow access to more potential binding sites with the ability to retain their potency against resistant cancers and viral strains since they can "wiggle and jiggle" in the binding site. These findings are causing a paradigm shift in drug design having anticancer and antiviral activity.

In one aspect, the present invention provides for a series of doubly flexible nucleoside analogues based on the acyclic nucleosides and the flex-base moiety found in the fleximers selected from compounds according to the following:

$R_1$ =

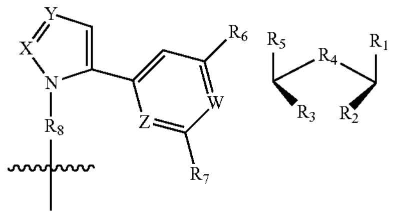

-continued

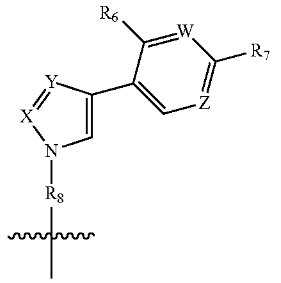

$R_2$ = H, $CH_2OH$, $CH_3$
$R_3$ = H, $CH_2OH$
$R_4$ = O, $CH_2$, NH
$R_5$ = H, OH, $CH_2OH$, $PO_3H_2$
$R_6$ = H, OH, $OCH_3$, OAc, OBn, $NH_2$, NHAc
$R_7$ = H, OH, $OCH_3$, OAc, OBn, $NH_2$, NHAc
$R_8$ = ——, $CH_2$
W = CH, N
X = CH, N
Y = CH, N
Z = CH, N or pharmaceutically acceptable salt, isomer, hydrate, prodrug or solvate thereof.

In another aspect the present invention provides for nucleoside analogues based on the acyclic nucleoside acyclovir (ACV) selected from the following compounds:

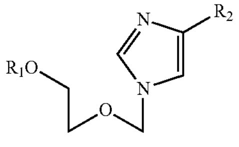

Wherein $R_1$ is H or $CH_3(C{=}O)$ and $R_2$ is a, b, c, d, e or f

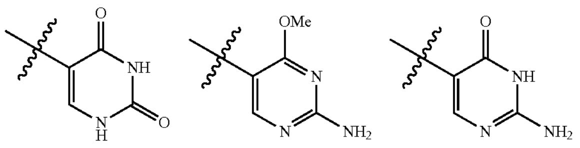

a b c

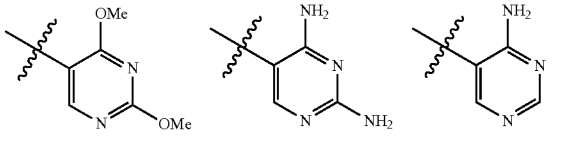

d e f or a pharmaceutically acceptable salt, isomer, hydrate, prodrug or solvate thereof.

More specifically, a nucleoside analogue based on the acyclic nucleoside acyclovir (ACV) is selected from the following compounds the ACV

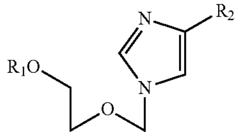

1 $R_1$ = H, $R_2$ = a
2 $R_1$ = H, $R_2$ = b
3 $R_1$ = H, $R_2$ = c
15 $R_1$ = H, $R_2$ = d
16 $R_1$ = H, $R_2$ = e
17 $R_1$ = H, $R_2$ = f
19 $R_1$ = Ac. $R_2$ = b

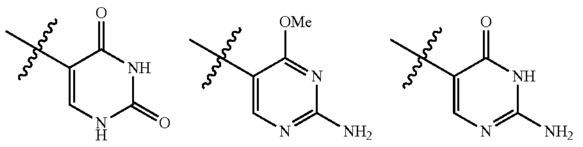

a b c

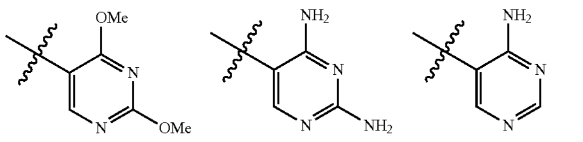

d e f wherein Ac is $CH_3(C{=}O)$, or a pharmaceutically acceptable salt, isomer, hydrate, prodrug or solvate thereof.

In yet another aspect, the present invention provides for a nucleoside analogue based on the acyclic nucleoside acyclovir selected from the following compounds:

1

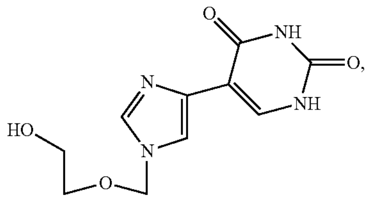

2

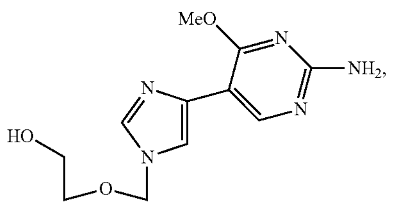

3

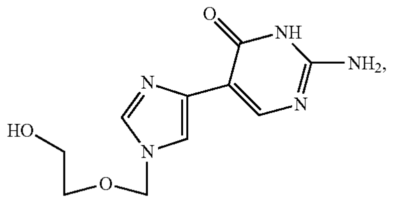

-continued

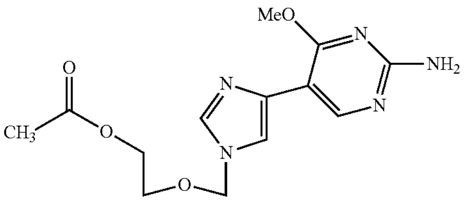

19 or a pharmaceutically acceptable salt, isomer, hydrate, prodrug or solvate thereof.

In another aspect, the present invention provides for the use of modified nucleosides of the present invention for medicine. In a more specific embodiment hereof, said use as a medicine is for the prevention or treatment of a coronavirus, SARS and MERS-CoV, more specifically for the prevention or treatment of an infection of a coronavirus, SARS and/or MERS-CoV in a subject, mammal or human.

In yet another aspect, the present invention provides for a method of treating, reducing or preventing the effects of a coronavirus in a subject in need of such therapy, the method comprising administering a therapeutically effective amount of a compound selected from the group consisting of

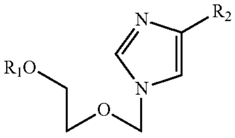

Wherein $R_1$ is H or $CH_3(C{=}O)$ and $R_2$ is a, b, c, d, e or f

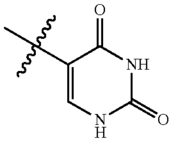

a

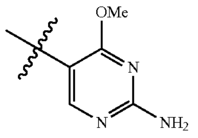

b

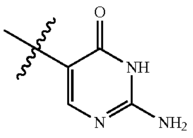

c

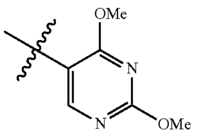

d

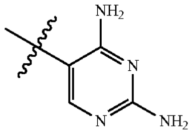

e

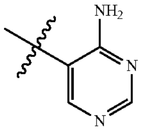

f or a pharmaceutically acceptable salt, isomer, hydrate, prodrug or solvate thereof.

More specifically, the method of treating, reducing or preventing the effects of a coronavirus in a subject in need of such therapy includes administering a therapeutically effective amount of a nucleoside analogue based on the acyclic nucleoside acyclovir (ACV) selected from the following compounds:

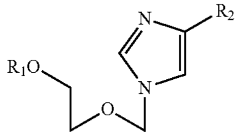

1 $R_1$ = H, $R_2$ = a
2 $R_1$ = H, $R_2$ = b
3 $R_1$ = H, $R_2$ = c
15 $R_1$ = H, $R_2$ = d
16 $R_1$ = H, $R_2$ = e
17 $R_1$ = H, $R_2$ = f
19 $R_1$ = Ac. $R_2$ = b

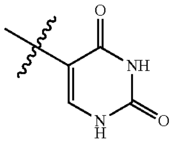

a

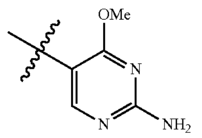

b

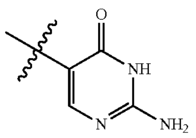

c

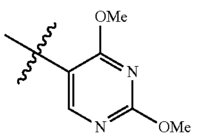

d

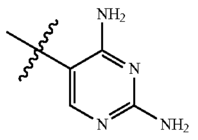

e

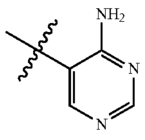

f wherein Ac is $CH_3(C{=}O)$, or a pharmaceutically acceptable salt, isomer, hydrate, prodrug or solvate thereof; and still more specifically the method of treating, reducing or preventing the effects of a coronavirus in a subject in need of such therapy comprises administering a therapeutically effective amount of a compound selected from the group consisting of:

1

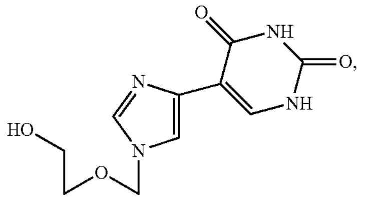

2

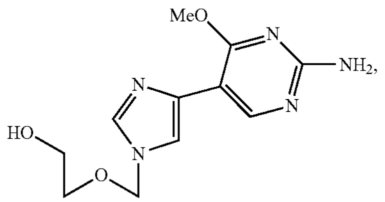

3

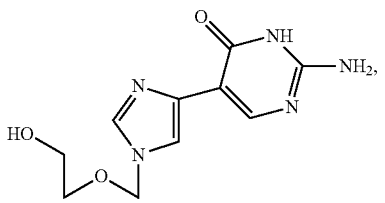

-continued

19

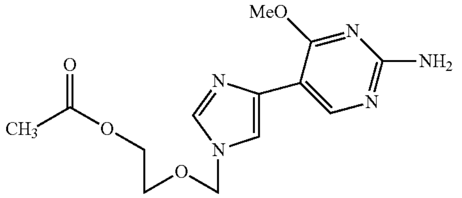

or a pharmaceutically acceptable salt, isomer, hydrate, prodrug or solvate thereof.

Preferably, a therapeutically effective amount of the acyclic fleximer nucleoside analogue is from 0.05 to 50 mg per kilogram body weight of the subject per day.

In a still further aspect, the present invention provides for a method of binding to both natural and mutated polymerases of a coronavirus, the method comprising administering a therapeutic amount of a modified nucleoside inhibitor, wherein the modified nucleoside is selected from the group consisting of:

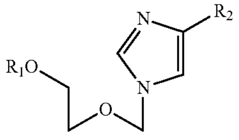

Wherein $R_1$ is H or $CH_3(C{=}O)$ and $R_2$ is a, b, c, d, e or f

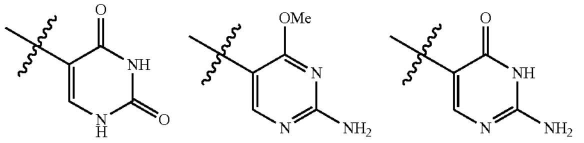

a b c

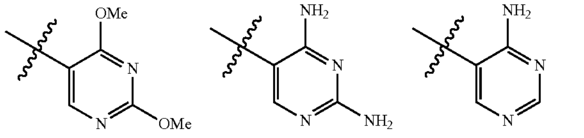

d e f or a pharmaceutically acceptable salt, isomer, hydrate, prodrug or solvate thereof;

and more specifically the method of binding to both natural and mutated polymerases of a coronavirus, comprises a compound selected from the group consisting of:

1

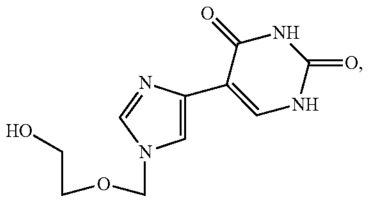

-continued

2

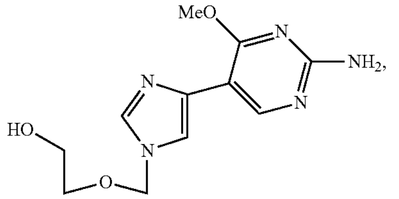

3

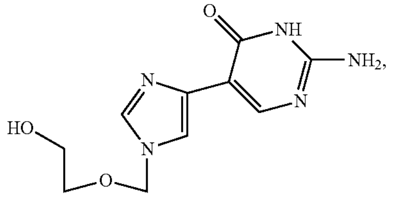

19

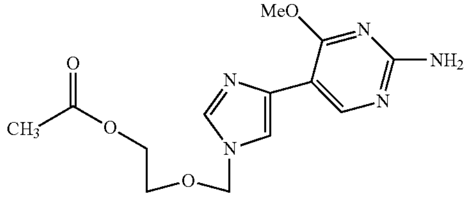

and a pharmaceutically acceptable salt, isomer, hydrate, prodrug or solvate thereof.

In yet another aspect, the present invention provides for contacting a cell infected with a coronavirus or to be infected with a coronavirus with at least one of the modified nucleosides provided herein, wherein the amount of the modified nucleosides is from about 1 μg/ml to about 40 μg/ml, and more preferably, from about 3 μg/ml to about 20 μg/ml.

In another aspect, the present invention provides for the manufacture of a medicament comprising the modified nucleosides of the present invention for the treatment of a coronavirus, SARS and MERS-CoV.

In another aspect, the present invention provides for the use of the modified nucleosides of the present invention for the prevention or treatment of a coronavirus, SARS and MERS-CoV, more specifically for the prevention or treatment of an infection of a coronavirus, SARS and/or MERS-CoV in a subject, mammal or human.

In yet another aspect, the present invention provides for a pharmaceutical composition comprising at least one of the modified nucleosides of the present invention and a pharmaceutically acceptable carrier.

In a still further aspect, the present application provides for a method of treating CoV in a patient, comprising administering to said patient a therapeutically effective amount of a compound of the present invention, and at least one additional therapeutic agent having anti-CoV properties.

In another aspect, the invention also provides a method of inhibiting CoV, comprising administering to a mammal infected with CoV a compound selected from compounds 2 and 19 and pharmaceutically effective salts thereof in an amount to effectively inhibit the replication of CoV in infected cells in the mammal.

In yet another aspect, the invention also provides novel intermediates or prodrugs which are useful for preparing the compounds of the invention or converted to active agents in vivo, respectively. Prodrugs are selected and prepared in order to improve some selected property of the molecule, such as water solubility or ability to cross a membrane, temporarily. Most common (biologically labile) functional groups utilized in prodrug design include carbonates, esters, amino acyl esters, amides, carbamates, oximes, imines, ethers or phosphates.

In other aspects, novel methods for synthesis, analysis, separation, isolation, purification, characterization, and testing of the compounds of this invention are provided.

DETAILED DESCRIPTION OF THE INVENTION

In designing the target molecules the flex-base modification of the fleximers was combined with the acyclic sugar moiety of acyclovir (ACV). ACV is a nucleoside polymerase inhibitor currently approved for the treatment of herpes simplex virus (HSV) and varicella zoster virus (VZV) infections.(18) Recently, it was also found to have activity against human immunodeficiency virus (HIV) when McGuigan's ProTide technology was employed.(19) It was found to suppress the replication of both HIV-1 and HSV-2 in the submicromolar range in lymphoid and cervicovaginal human tissues and at 3-12 μmol/L in $CD4^{+}$ T cells. (19)

Unique nucleoside analogues have been termed 'fleximers' and were designed to explore how nucleobase flexibility affects the recognition, binding, and activity of nucleoside(tide) analogues. (11-16) The fleximers possess a purine base scaffold in which the imidazole and pyrimidine moieties are attached by a single carbon-carbon bond, rather than being 'fused' as is typical for the purines. These analogues are designed to retain all of the requisite purine hydrogen bonding patterns while allowing the nucleobase to explore alternative binding modes. Previous work from the present inventors include flexible analogues have several strategic advantages, such as increased binding affinity compared to the corresponding rigid inhibitors, binding affinity to atypical enzymes, as well as the ability to overcome point mutations in biologically significant binding sites.(11, 12, 17)

The present invention provides for a series of doubly flexible nucleoside analogues based on the acyclic sugar scaffold of acyclovir and the flex-base moiety found in the fleximers. The target compounds were evaluated for their antiviral potential and found to inhibit several coronaviruses. Significantly, several of the compounds displayed selective antiviral activity (CC50>3×EC50) towards human coronavirus (HCoV)-NL63, Middle East respiratory syndrome-coronavirus (MERS-CoV) and severe acute respiratory syndrome-coronavirus (SARS-CoV). In the case of HCoV-NL63 the activity was highly promising with an EC50<10 μM and a CC50>100 μM. As such, these doubly flexible nucleoside analogues described herein are viewed as a novel new class of drug candidates for potent inhibition of coronaviruses.

Mammal or human hosts infected with a coronavirus can be treated by administering to said mammal or human an effective amount of an acyclic fleximer nucleoside analogue of the present invention and such compounds can be administered by any appropriate route, for example, orally, parenterally, intravenously, intradermally, subcutaneously, or topically, in liquid or solid form.

The present invention relates to a method for treating a CoV viral infection, comprising the administration, to a patient, of an effective amount of at least one acyclic fleximer nucleoside analogue of the present invention and/or of a composition containing same. In general, the acyclic fleximer nucleoside analogues, as active agents, of this invention will be administered in a therapeutically effective amount by any of the accepted modes of administration for agents that serve similar utilities. The effective amount will be that amount of an acyclic fleximer nucleoside analogue of the present invention that would be understood by one skilled in the art to provide therapeutic benefits. The active agent can be administered once a week, twice or more times per week, once a day, or more than once a day. As indicated above, all of the factors to be considered in determining the effective amount will be well within the skill of the attending clinician or other health care professional.

For example, therapeutically effective amounts of an acyclic fleximer nucleoside analogue of the present invention may range from approximately 0.05 to 50 mg per kilogram body weight of the subject per day; preferably about 0.1-25 mg/kg/day, more preferably from about 0.5 to 10 mg/kg/day. Thus, for administration to a 70 kg person, the dosage range would most preferably be about 35-700 mg per day.

In general, an acyclic fleximer nucleoside analogue of the present invention can be administered as pharmaceutical compositions by any one of the following routes: oral, systemic (e.g., transdermal, intranasal or by suppository), or parenteral (e.g., intramuscular, intravenous or subcutaneous) administration. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration and bioavailability of the acyclic fleximer nucleoside analogue. For delivery via inhalation the compound can be formulated as liquid solution, suspensions, aerosol propellants or dry powder and loaded into a suitable dispenser for administration.

A composition comprising an acyclic fleximer nucleoside analogue of the present invention may be combined with at least one pharmaceutically acceptable carrier, excipient or diluent. Some examples of acceptable excipients are those that are non-toxic, will aid administration, and do not adversely affect the therapeutic benefit of the compound of the invention. Such excipient may be any solid, liquid, semi-solid or, in the case of an aerosol composition, gaseous excipient that is generally available to one of skill in the art.

Solid pharmaceutical excipients useful in the invention may include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990). The amount of an acyclic fleximer nucleoside analogue of the present invention can vary within the full range employed by those skilled in the art. For example, a composition may contain, on a weight percent (wt %) basis, from about 0.01-99.99 wt % of an acyclic fleximer nucleoside analogue of the present invention based on the total formulation, with the balance being one or more suitable pharmaceutical excipients.

The pharmaceutical composition according to the invention preferably comprises an amount of an acyclic fleximer nucleoside analogue of the present invention of between 5 μg and 1000 mg, preferably between 1 and 500 mg, preferably between 5 and 100 mg. The ratio between the amounts by weight of an acyclic fleximer nucleoside analogue of the present invention and of pharmaceutically acceptable carrier is between 5/95 and 95/5, preferably between 20/80 and 80/20.

The acyclic fleximer nucleoside analogues of the present invention may be the only active ingredients, or they may be combined with other active ingredients. The pharmaceutical composition according to the invention may thus also comprise at least one other pharmaceutical active agent, in particular at least one other medicament used for the treatment of viral infection. In particular, the composition according to the invention may also comprise, or be combined with, one or more other antivirals. Generally, any antiretroviral may be combined, namely reverse transcriptase inhibitors, in particular nucleoside or nucleotide and non-nucleoside inhibitors, protease inhibitors, entry inhibitors, integrase inhibitors, etc.

The acyclic fleximer nucleoside analogues of the present invention or compositions comprising same may be administered in various ways and in various forms. Thus, they may be administered systemically, orally, by inhalation or by injection, for instance intravenously, intramuscularly, subcutaneously, transdermally, intra-arterially, etc., intravenous, intramuscular, subcutaneous and oral administration. For the injections, the acyclic fleximer nucleoside analogues of the present invention are generally conditioned in the form of liquid suspensions, which can be injected by means of syringes or infusions, for example. In this regard, the acyclic fleximer nucleoside analogues of the present invention are generally dissolved in buffered, isotonic, physiological, saline, etc., solutions which are compatible with pharmaceutical use and known to those skilled in the art. Thus, the compositions may contain one or more agents or carriers chosen from dispersants, solubilizing agents, stabilizers, preservatives, etc. Agents or carriers which can be used in liquid and/or injectable formulations are, in particular, methylcellulose, hydroxymethylcellulose, carboxymethylcellulose, polysorbate 80, mannitol, gelatin, lactose, vegetable oils, acacia, etc.

The acyclic fleximer nucleoside analogues of the present invention can also be administered in the form of gels, oils, tablets, suppositories, powders, gel capsules, capsules, aerosols, etc. For this type of formulation, an agent such as cellulose, carbonates or starches is advantageously used.

Generally, for the purpose of the present invention, solvates of pharmaceutically acceptable solvents such as water and ethanol are equivalent to those not in forms of solvates.

The present invention relates to a method for treating a CoV viral infection, comprising the administration, to a patient, of an effective amount of at least one acyclic fleximer nucleoside analogue of the present invention and/or of a composition containing same. The acyclic fleximer nucleoside analogue can further be prodrugs or in form of capable of releasing the active ingredient after in vivo metabolism.

EXAMPLES

In approaching the synthesis of the above described analogues a previously published route was used to the acyclic sugar moiety and then utilized a series of organometallic coupling techniques in order to construct the flexible base. Specifically, as shown below in Scheme, the route to compound 8 involved coupling 2-aceteoxyethyl acetoxymethylether (4), synthesized according to published procedures, (20) to diiodoimidazole using modified Vorbruggen conditions.(20) This was followed by removal of the more labile acetate protecting group and subsequent protection with the more robust benzyl. Then, selective deiodination of the C5-iodo with EtMgBr yielded key intermediate compound 8.

Scheme 1.

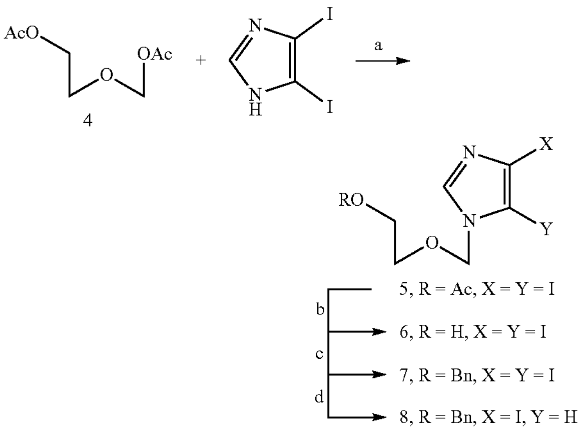

4

5, R = Ac, X = Y = I

6, R = H, X = Y = I

7, R = Bn, X = Y = I

8, R = Bn, X = I, Y = H

Reagents and conditions: (a) N,O-bis(trimethylsilyl)acetamide, acetonitrile, TMSOTf; (b) $NH_4OH$, EtOH; (c) $Bu_4NI$, NaH, BnBr; (d) EtMgBr, anhydrous DMF.

This product served as a key intermediate for a series of organometallic coupling reactions. The first coupling partner selected was the boronic acid derivative of 2,4-dibenzyluracil (9). This analogue was chosen due to the versatility of compound 10. As had been previously published (13) it was hypothesized it would be possible to obtain both the Flex-xanthosine and Flex-guanosine analogues from compound 10, as shown in Scheme 2. Preparation of the boronic acid compound 9 followed established procedures (21) and was used immediately without further characterization. Using standard Suzuki reaction conditions in the presence of freshly prepared $Pd(PPh_3)$ compounds 4 and 10 were obtained in a 45% yield. In order to obtain the xanthosine analogue, compound 10 was treated with Pd/C to remove the benzyl protecting groups to yield final compound 1 in a 26% yield. It was also discovered that by lowering the temperature of the reaction, the benzyl groups could be selectively removed from the base. This is convenient, as it would allow for future functionalization of compound 11 without the need to selectively reprotect the free hydroxyl.

Scheme 2.

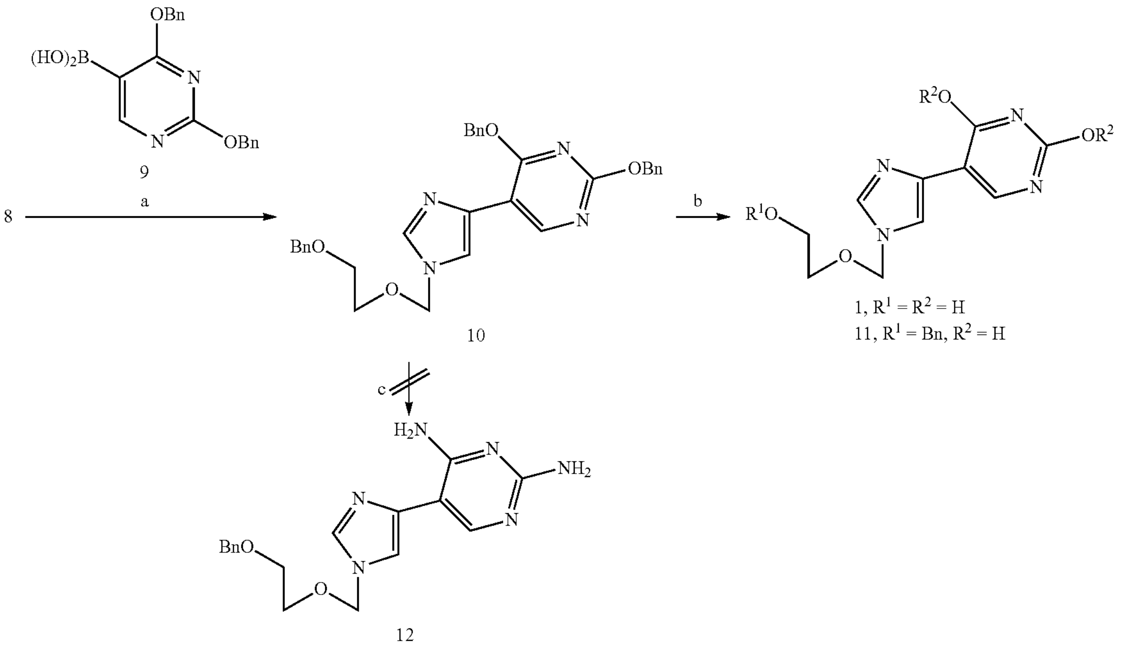

8, 9, 10, 12

1, $R^1 = R^2 = H$

11, $R^1$ = Bn, $R^2 = H$

Reagents and conditions: (a) $Pd(PPh_3)_4$, $NaHCO_3$, dimethoxyethane; (b) Pd/C, ammonium formate, EtOH, for 1: 120 C., 18 h, for 11: 60 C. for 18 h; (c) methanolic ammonia, 210 C.

In an attempt to obtain the guanosine analogue, compound 10 was treated with methanolic ammonia under pressure, at 210 C to yield the intermediate diamino compound 12. Unfortunately, the reaction resulted in a single site transformation at the 4-position. Due to extreme reaction conditions and low yield this route was abandoned. Ultimately, the guanosine analogues were obtained through Stille coupling of key intermediate compound 8 with the appropriate pyrimidine compound 13. Pyrimidine 13 was prepared from commercially available 2-amino-5-chloro-6-methoxy pyrimidine according to published procedures. The subsequent coupling was completed using modified Stille coupling conditions based on the findings of Mee et al.(22)

In order to acquire final compound 2, a selective deprotection was used to remove the benzyl group, while leaving the 6-methoxy intact. This was done with Pd/C in the presence of ammonium formate in EtOH under reflux for 18 h. This yielded compound 2 in a 24% yield, with the remainder (52%) retrievable as starting material, which could be recycled. The final deprotection was accomplished with $BBr_3$ at room temperature to yield compound 3 in a 24% yield as shown below in Scheme 3.

Scheme 3.

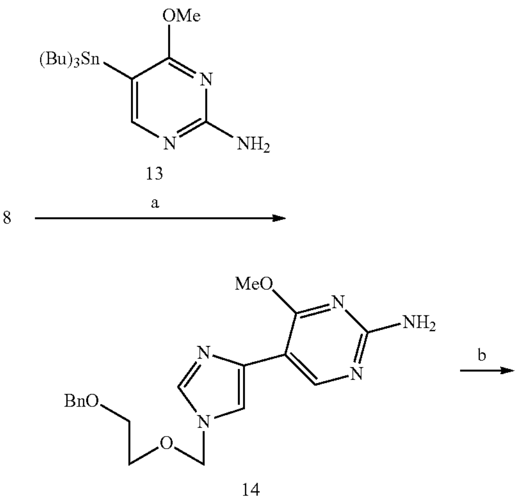

13, 8, 14

-continued

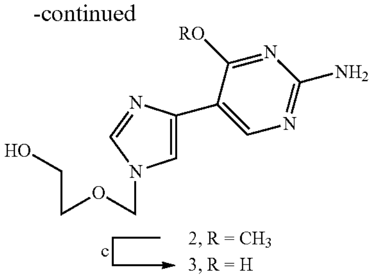

2, $R = CH_3$
3, $R = H$

Reagents and conditions: (a) $Pd(PPh_3)_4$, CuI, TBAF, DMF, 45° C., 18 h; (b) Pd/C, ammonium formate, EtOH, 120 C., 18 h; (c) $BBr_3$.

Scheme 4.

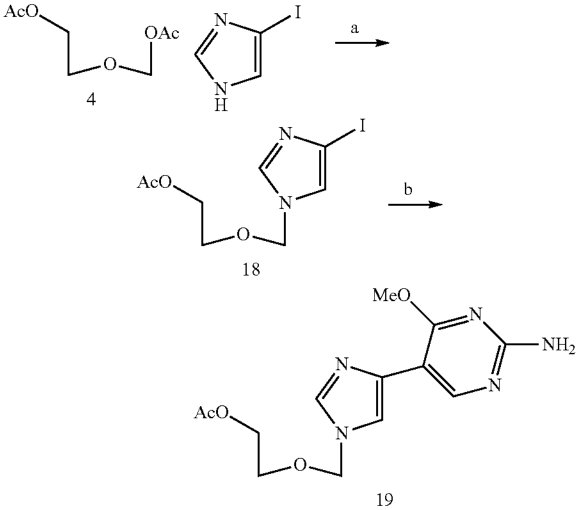

4

18

19

Reagents and conditions: (a) BSA, TMSOTf, MeCN, 80° C.; (b) $Pd(PPh)_2Cl_2$, CuI, TBAF, THF, 60° C.

The effect of numerous target fleximer analogues on the replication of HCoV-NL63 was evaluated. HCoV-NL63 infection does not result in full cytopathy in the Vero-118 cell culture model used. For this reason, the antiviral effect was analyzed microscopically by scoring virus-induced cytopathogenic effects (CPE) in each well on a scale of 1 (mild) to 5 (severe). These scores were then used to calculate the percentage of inhibition by normalization to control wells.

As shown in Table 1, in contrast to acyclovir, one of the tested nucleosides, nucleoside 2, demonstrated selective antiviral activity (CC50>10×).

TABLE 1

Antiviral activity of nucleoside analogues

| | HCoV-NL63 in Vero118 | | MERS-CoV in Huh7 | | MERS-CoV in Vero | | SARS-CoV in VeroE6 | |
|---|---|---|---|---|---|---|---|---|
| Cmpd. | EC50[a] | CC50[b] | EC50[a] | CC50[b] | EC50[a] | CC50[b] | EC50[a] | CC50[b] |
| 1 | 92 ± 68 | >200 | ND[c] | ND[c] | ND[c] | ND[c] | ND[c] | ND[c] |
| 2 | 8.8 ± 1.5 | 120 ± 37 | 13.5 ± 0.0 | 54.0 ± 1.7 | 10.1 ± 1.2 | 77.2 ± 50.1 | 28.1 ± 0.2 | 90.8 ± 7.1 |
| 3 | >200 | >200 | ND[c] | ND[c] | ND[c] | ND[c] | ND[c] | ND[c] |
| Acyclovir | >100 | >100 | >1000 | >1000 | >1000 | >1000 | >1000 | >1000 |
| 17 | ND[c] | ND[c] | 116.2 ± 8.6 | >400 | 71.3 ± 1.6 | 359.3 ± 95.4 | 172.1 ± 41.4 | >400 |
| 19 | ND[c] | ND[c] | 5.3 ± 0.7 | 23.4 ± 0.4 | 3.4 ± 0.3 | 17.3 ± 4.8 | 11.9 ± 0.2 | 35.0 ± 7.1 |

[a]EC50: Effective concentration showing 50% inhibition of virus-induced CPE (in μM).

[b]CC50: Cytotoxic concentration showing 50% inhibition of cell survival (in μM).

[c]ND: Not determined.

Based on these results the activity of nucleoside compound 2 was also evaluated on the more pathogenic viruses MERS-CoV and SARS-CoV. Infection of Huh7 and Vero cells with MERS-CoV and Vero cells with SARS-CoV resulted in complete CPE. This allowed for the quantification of the antiviral effect by using a commercial cell viability assay as described previously.(23-24) Inhibition of virus-induced CPE (i.e., enhanced cell viability compared to untreated, virus-infected cells) was determined in the presence of different compound concentrations. The results depicted in Table 1 indicate that compound 2 can block the replication of MERS-CoV but not SARS-CoV while acyclovir had no effect (Table 1).

The effect of compound 2 on HCoV-NL63 is significant with an EC50<10 μM and a CC50>100 μM. The results showed that compound 2 reduced the viability of different cell lines at different concentrations suggesting a cell-specific effect. The different sensitivity of the cell lines towards this nucleoside could be caused by differences in growth rate, compound uptake and metabolism, or other cell line-specific characteristics. Notably compound 19 can block the replication of MERS-CoV and SARS-CoV had an EC50<12 μM and a CC50 almost three (3) times the EC50.

The present invention provides for the design, synthesis and screening of a series of novel nucleoside analogues that employ a strategy of combining the flex-base motif with the flexible acyclic sugar scaffold of the FDA-approved drug acyclovir. The results herein show that this approach produces medicinally relevant molecules capable of inhibiting HCoV-NL63, MERS-CoV and SARS-CoV replication in cell culture. Although the parental compound, acyclovir, serves as a polymerase inhibitor, (25-26) it is yet unclear how these novel analogues disrupt viral replication although it is theorized that such polymerase inhibitor activity is relevant to the current compounds.

Moreover, a comparison of the activity profiles of compounds 2 and 3 indicates that the methoxy group of compound 2 may be serving as a prodrug, as has been established in other antiviral nucleoside analogues.(27)

Methods and Materials

All chemicals and reagents listed in this section were purchased through commercially available sources unless otherwise noted. All reactions run in $CH_2Cl_2$, $CH_3CN$, and THF were obtained from a solvent purification system (SPS, Model: mBraun Labmaster 130). All reactions run in anhydrous DMF, $CH_3OH$ and pyridine were obtained from Sigma-Aldrich or Acros Organics. All $^1H$ and $^{13}C$ NMR spectra were obtained from a JEOL ECX 400 MHz NMR. All $^1H$ NMR spectra were referenced to internal tetramethylsilane (TMS) at 0.0 ppm. The spin multiplicities are indicated by the symbols s (singlet), d (doublet), dd (doublet of doublets), t (triplet), q (quartet), m (multiplet), and br (broad). All reactions were monitored by thin layer chromatography (TLC) on 0.25 mm precoated glass plates. All flash column chromatography was run on a Teledyne Isco Combiflash Rf system. Purity of the tested compounds was >95% based on LC, HRMS and $^1H$ NMR unless otherwise stated. Melting points are uncorrected. All mass spectra (MS) were recorded and obtained from the Johns Hopkins Mass Spectrometry Facility. The FAB mass spectra were obtained using double focusing magnetic sector mass spectrometer equipped with a Cs ion gun and fourier transform ion cyclotron resonance equipped with ESI source.

2-((4,5-diiodo-1H-imidazol-1-yl)methoxy)ethyl acetate (Compound 5) 4,5-Diiodoimadazole (15.1 g, 47 mmol) and 2-aceteoxyethyl acetoxymethylether (Compound 4, 10.0 g, 57 mmol) were dissolved in anhydrous acetonitrile (150 mL) under inert atmosphere. N,O-bis(trimethylsilyl) acetamide (70.0 mL, 284 mmol) was added. The reaction mixture was stirred at rt for 5 h, and then cooled to 0° C. Trimethylsilyl triflouromethane sulfonate (14.0 mL, 71 mmol) was added slowly and then the solution was heated to 90° C. and stirred for 12 h. The reaction mixture was quenched by addition of aq. $NaHCO_3$ (30 mL) and stirred for 30 min. The solution was separated and the aqueous layer was extracted with $CH_2Cl_2$ (2×50 mL). The organic layers were combined, washed with $H_2O$ (3×50 mL) and brine (50 mL), and dried over $MgSO_4$. The solvent was removed under reduced pressure. The resultant syrup was purified by flash chromatography over silica gel to obtain colorless solid compound 5. (11.6 g, 47%). $^1H$ NMR ($CDCl_3$, 400 MHz): δ 7.73 (1H, s), 5.35 (2H, s), 4.19 (2H, t, J=4.6 Hz), 3.64 (2H, t, J=4.6 Hz), 2.06 (3H, s). $^{13}C$ NMR ($CDCl_3$, 100 MHz): δ 170.9, 141.8, 97.5, 81.9, 78.1, 66.9, 62.8, 21.0. HRMS calcd for $C_8H_{10}I_2N_2O_3$ 436.8859, found 436.8860 [M+H$^+$].

2-((4,5-diiodo-1H-imidazol-1-yl)methoxy)ethan-1-ol (Compound 6) Compound 5 (11.6 g, 27 mmol) was dissolved in ethanol (100 mL). $NH_4OH$ was added slowly until signs of precipitation occurred. The reaction mixture stirred at rt for 16 hr. The majority of solvent was removed via air stream to produce light yellow slurry. The solid was filtered off and washed with ice cold $H_2O$ (50 mL) to yield light yellow solid compound 6 (7.8 g, 74%). Mp 122.8-124.1° C.; $^1H$ NMR ($CDCl_3$, 400 MHz): δ 7.74 (1H, s), 5.38 (2H, s), 3.75 (2H, t, J=4.56), 3.56 (2H, t, J=4.56). $^{13}C$ NMR ($CDCl_3$, 100 MHz): δ 141.8, 97.5, 81.9, 78.2, 70.1, 61.6. HRMS calcd for $C_6H_8I_2N_2O_2$ 394.8753, found 394.8755 [M+H$^+$].

1-((2-(benzyloxy)ethoxy)methyl)-4,5-diiodo-1H-imidazole (Compound 7) Sodium hydride (95%, 0.91 g, 38 mmol) was added to a stirred solution of compound 6 (10.0 g, 25 mmol) in anhydrous THF (150 mL) at 0° C. under inert atmosphere. The mixture was stirred at room temperature for 3 h. Tetrabutylammonium iodide (2.3 g, 6 mmol) and benzyl bromide (4.5 mL, 38 mmol) was added. The mixture was stirred at room temperature for 12 h, followed by quenching with ethanol (20 mL). The solvent was removed under reduced pressure; $H_2O$ (200 mL) was added and the mixture extracted with $CH_2Cl_2$ (3×100 mL). The organic extracts were combined, washed with brine (200 mL), and dried over $MgSO_4$. The solvent was removed under reduced pressure to give a pale brown syrup. Flash chromatography over silica gel gave compound 7 as a colorless syrup (8.5 g, 70%). $^1H$ NMR ($CDCl_3$, 400 MHz): δ 7.72 (1H, s), 7.31-7.34 (5H, m), 5.38 (2H, s), 4.53 (2H, s), 3.61 (4H, s). $^{13}C$ NMR ($CDCl_3$, 100 MHz): δ 142.0, 137.8, 128.6, 127.94, 127.88, 97.3, 81.9, 78.3, 73.6, 69.4, 68.1. HRMS calcd for $C_{13}H_{14}I_2N_2O_2$484.9223, found 484.9225 [M+H$^+$].

1-((2-(benzyloxy)ethoxy)methyl)-4-iodo-1H-imidazole (Compound 8) Compound 7 (10.0 g, 25 mmol) was dissolved in anhydrous THF (50 mL) under inert atmosphere. The reaction mixture was taken to −15° C. and EtMgBr (1.7 mL 3M in THF, 5.0 mmol) was added dropwise in two portions 30 min apart. The solution was allowed to come to rt and stirred for 4 hr. The reaction was quenched by addition of aq. sat. $NH_4Cl$ (20 mL). The solution was separated and the aqueous layer was extracted with $CH_2Cl_2$ (3×20 mL). The organic layers were combined, washed brine (20 mL), and dried over $MgSO_4$. The solvent was removed under reduced pressure. The resultant syrup was purified by flash chromatography over silica gel to obtain yellow syrup compound 8 (7.0 g, 78%). $^1H$ NMR ($CDCl_3$, 400 MHz): δ 7.48 (1H, d, J=1.36), 7.28-7.34 (5H, m), 7.13 (1H, d, J=1.36), 5.29 (2H, s), 4.52 (2H, s), 3.55-3.61 (4H, m). $^{13}C$ NMR ($CDCl_3$, 100 MHz): δ 138.9, 137.8, 128.6, 127.9, 127.8, 124.6, 82.9, 76.6, 73.5, 69.3, 68.1. HRMS calcd for $C_{13}H_{15}IN_2O_2$ 359.0256, found 359.0257 [M+H$^+$].

2,4-bis(benzyloxy)-5-(1-((2-(benzyloxy)ethoxy)methyl)-1H-imidazol-4-yl)pyrimidine (Compound 10) A mixture of compound 8 (75.2 mg, 0.21 mmol) and compound 9 (100 mg, 0.28 mmol) and $Pd(PPh_3)_4$ (33 mg, 0.028 mmol) in DME (5 mL) was stirred at r.t. under argon for 10 min. To this mixture was added compound 9 (103 mg, 0.03 1 mmol) in DME (5 mL). Sat. aq $NaHCO_3$ (10 mL) was added and the mixture refluxed under argon for 4 h. The soln was cooled to r.t. and the DME layer separated and set aside. The aqueous layer was then extracted with EtOAc (3×25 mL), and the organic extracts were combined with the DME layer, washed with brine (50 mL), and dried over $MgSO_4$. The solvent was removed under reduced pressure to give a pale brown syrup. Flash chromatography over silica gel gave compound 10 (30 mg, 21%) as a yellow syrup. $^1$H NMR ($CDCl_3$, 400 MHz): δ 9.07 (1H, s), 7.62-7.69 (5H, m), 7.41-7.49 (5H, m), 7.27-7.38 (5H, m), 5.53 (2H, s), 5.45 (2H, s), 5.31 (2H, s), 4.5 (2H, s) 3.52-3.58 (4H, m). $^{13}$C NMR ($CDCl_3$, 100 MHz): δ 166.3, 163.1, 156.2, 137.9, 137.3, 136.8, 136.3, 134.5, 133.1, 132.2, 132.1, 132.04, 132.03, 128.72, 128.67, 128.54, 128.50, 128.4, 128.2, 128.1, 128.0, 127.9, 127.8, 118.3, 109.6, 76.8, 73.4, 69.3, 69.2, 68.8, 68.0. HRMS calcd for $C_{31}H_{30}N_4O_4$ 523.2345, found 523.2335 [M+H$^+$].

5-(1-((2-hydroxyethoxy)methyl)-1H-imidazol-4-yl)pyrimidine-2,4-diol (Compound 1) A mixture of compound 10 (30 mg, 0.06 mmol), 10% Pd/C (60 mg), and ammonium formate (38 mg, 0.06 mmol) in EtOH (10 mL) was heated under reflux for 18 h. The mixture was filtered through Celite and the Celite pad was washed several times with hot EtOH. The combined filtrate was evaporated under reduced pressure. The residue was purified by flash chromatography over silica gel to yield white solid compound 1 (9 mg, 60%). $^1$H NMR ($(CD_3)_2SO$, 400 MHz): δ 11.22 (1H, br), 10.94 (1H, br), 7.79 (1H, s), 7.76 (1H, s), 7.62 (1H, s), 5.34 (2H, s), 3.42 (2H, t, J=4.6), 3.36 (2H, t, J=4.6). $^{13}$C NMR ($(CD_3)_2SO$, 100 MHz): δ 162.9, 151.1, 138.0, 136.4, 134.0, 117.4, 107.8, 76.2, 70.4, 60.4. HRMS calcd for $C_{10}H_{12}N_4O_4$253.0937, found 253.0938 [M+H$^+$].

5-(1-((2-(benzyloxy)ethoxy)methyl)-1H-imidazol-4-yl)pyrimidine-2,4-diol (Compound 11) The title compound was prepared from compound 10 in the same manner as described above altering only the temperature of the reaction to 60° C. Yield 35%, white solid. $^1$H NMR ($(CD_3)_2SO_4$, 400 MHz): δ 11.22 (1H, br), 10.94 (1H, br), 7.79 (1H, s), 7.76 (1H, d, 0.92), 7.63 (1H, d, J=0.92), 7.22-7.32 (5H, m), 5.35 (2H, s), 4.42 (2H, s), 3.51 (4H, m). $^{13}$C NMR ($(CD_3)_2SO_4$, 100 MHz): δ 162.7, 150.9, 138.9, 138.0, 136.4, 134.0, 128.8, 128.0, 127.9, 117.2, 107.8, 76.1, 72.5, 69.2, 68.0. HRMS calcd for $C_{17}H_{18}N_4O_4$343.1406, found 343.1407 [M+H$^+$].

5-(1-((2-(benzyloxy)ethoxy)methyl)-1H-imidazol-4-yl)-4-methoxypyrimidin-2-amine (Compound 14) A mixture of compound 8 (233 mg, 0.65 mmol), compound 13 (350 mg, 0.84 mmol), $Pd(PPh_3)_4$ (23 mg, 0.05 mmol), CuI, (23 mg, 0.12 mmol), and tetrabutyl ammonium fluoride trihydrate (410 mg, 1.3 mmol) in anhydrous DMF (10 mL) was heated at 45° C. for 18 h. The mixture was filtered through Celite and diluted with EtOAc (5 mL), washed with brine, and dried over $MgSO_4$. The organic solvents were removed and the product was purified by flash chromatography to give compound 14 (96 mg, 42%) as a red oil. $^1$H NMR ($(CD_3)_2SO$, 400 MHz): δ 8.84 (1H, s), 7.79 (1H, s), 7.40 (1H, s), 7.20-30 (5H, m), 6.56 (2H, bs) 5.37 (2H, s), 4.41 (2H, s), 3.91 (3H, s) 3.50-3.55 (4H, m). $^{13}$C NMR ($(CD_3)_250$, 100 MHz): δ 165.8, 162.3, 155.5, 138.8, 138.1, 134.8, 128.7, 128.0, 127.9, 117.2, 104.7, 76.2, 72.6, 69.3, 67.9, 53.7. HRMS calcd $C_{18}H_{21}N_5O_3$356.1723, found 356.1729 [M+H$^+$].

2-((4-(2-amino-4-methoxypyrimidin-5-yl)-1H-imidazol-1-yl)methoxy)ethan-1-ol (Compound 2) A mixture of compound 14 (94 mg, 0.27 mmol), 10% Pd/C (60 mg), and ammonium formate (167 mg, 2.7 mmol) in EtOH (10 mL) was heated under reflux for 18 h. The mixture was filtered through Celite and the Celite pad was washed several times with hot EtOH. The combined filtrate was evaporated under reduced pressure. The residue was purified by flash chromatography over silica gel to yield pink syrup compound 2 (17 mg, 22%). $^1$H NMR ($CD_3OD$, 400 MHz): δ 8.54 (1H, s), 7.82 (1H, d, J=0.92), 7.51 (1H, d, J=0.92), 5.43 (2H, s), 4.02 (3H, s), 3.63 (2H, t, J=4.56), 3.51 (2H, t, J=4.56). $^{13}$C NMR ($CD_3OD$, 100 MHz): δ 166.4, 161.8, 153.8, 137.4, 134.2, 117.5, 104.8, 76.5, 70.0, 60.6, 52.8. HRMS calcd $C_{11}H_{17}N_5O_3$ 266.1253, found 266.1247 [M+H$^+$].

2-amino-5-(1-((2-hydroxyethoxy)methyl)-1H-imidazol-4-yl)pyrimidin-4(3H)-one (Compound 3) Compound 2 (9.0 mg, 0.034 mmol) was dissolved in anhydrous $CH_2Cl_2$ (5 mL) under inert atmosphere and brought to −78° C. $BBr_3$ (350 μL, 0.34 mmol) was added. The reaction mixture was stirred at rt 48 hr. Solvent removed by air stream. Residue was recrystallized in EtOH to produce white solid compound 3 (4.2 mg, 49%). $^1$H NMR ($(CD_3)_2SO_4$, 400 MHz): δ 9.19 (1H, br), 8.24 (1H, s), 8.06 (1H, s) 5.58 (2H, s), 3.48-3.52 (4H, m), 2.47. $^{13}$C NMR ($(CD_3)_2SO_4$, 100 MHz): δ 159.2, 154.2, 145.8, 136.2, 127.6, 118.2, 104.5, 78.4, 71.7, 60.3. HRMS calcd $C_{10}H_{13}N_5O_3$252.1097, found 252.1089 [M+H$^+$].

2-((4-iodo-1H-imidazol-1-yl)methoxy)ethyl acetate (Compound 18) 4(5)-Monoiodoimidazole (3.8 g, 19.3 mmol) and compound 4 (3.4, (4.1 g, 23.2 mmol) were dissolved in anhydrous $CH_3CN$ (150 mL) under inert atmosphere. N,O-bis(trimethylsilyl) acetamide (28.6 ml, 115.8 mmol) was added. The reaction mixture was stirred at rt for 5 h, and then cooled to 0° C. Trimethylsilyl triflouromethane sulfonate (5.7 mL, 25.6 mmol) was added slowly and then the solution was heated to 90° C. and stirred for 12 h. The reaction mixture was quenched by addition of aq. $NaHCO_3$ (30 mL) and stirred for 30 min. The solution was separated and the aqueous layer was extracted with $CH_2Cl_2$ (2×50 mL). The organic layers were combined, washed with $H_2O$ (3×50 mL) and brine (50 mL), and dried over $MgSO_4$. The solvent was removed under reduced pressure. The resultant syrup was purified by flash chromatography over silica gel to obtain yellow syrup 18. (346 mg, 6%). $^1$H NMR ($CDCl_3$, 400 MHz): δ 7.38 (1H, d, J=0.92 Hz), 7.01 (1H, d, J=0.88 Hz), 5.14 (2H, s), 3.95 (2H, t, J=4.6 Hz), 3.45 (2H, t, J=4.6 Hz) 1.84 (3H, s). $^{13}$C NMR ($CDCl_3$, 100 MHz): δ 170.8, 139.2, 124.6, 82.7, 76.4, 66.8, 62.8, 20.9. NMS calcd for $C_8H_{11}I1N_2O_3$ 310.9, found 311.0[M+H$^+$].

2-((4-(2-amino-4-methoxypyrimidin-5-yl)-1H-imidazol-1-yl)methoxy)ethyl acetate (Compound 19) A mixture of compound 18 (173 mg, 0.56 mmol), compound 13 (845 mg, 2.04 mmol), $PdCl_2(PPh_3)_2$ (143 mg, 0.2 mmol), CuI (143 mg), and TBAF.3$H_2O$ (1.0 g, 3.14 mmol) in anhydrous DMF (25 mL) was heated at 60° C. for 18 h. The mixture was filtered The product was dried on Celite and purified by flash chromatography to give 19 (51.6 mg, 30%) as a yellow oil. $^1$H NMR ($CD_3OD$, 400 MHz): δ 8.54 (1H, s), 7.84 (1H, s), 7.51 (1H, s), 5.42 (2H, s), 4.15 (2H, t, J=4.6 Hz), 4.03 (3H, s), 3.67 (2H, t, J=4.6 Hz), 1.97 (3H, s). $^{13}$C NMR ($CD_3OD$, 100 MHz): δ 171.3, 166.7, 161.7, 153.2, 137.2, 134.1, 117.6, 105.5, 76.4, 66.6, 62.9, 52.7, 19.3. NMS calcd $C_{13}H_{17}N_5O_4$308.1, found 308.3[M+H$^+$].

NL63-CoV Antiviral Assay.

This assay was performed as described previously.(28) Both the human coronavirus NL63 strain and the Vero118 cell line were kindly provided by Ron A. Fouchier (Erasmus Medical Center, Rotterdam, The Netherlands). The HCoV-NL63 strain was isolated from an 8 months old boy suffering from pneumonia.(29) A previously undescribed coronavirus associated with respiratory disease in humans. Vero-118 cells are a subclone of Vero-WHO cells(30), and were cultured in Iscove's Modified Dulbecco's Medium (Life Technologies, Gent, Belgium—cat no 21980-032) with 10% FBS, 100 IU penicillin/mL and 100 μg streptomycin/mL. Cells were split ¼ twice weekly. For the antiviral assay Vero-118 cells in 96-well plate format were infected with HCoV-NL63 (MOI=0.01, 200 μL cell culture, 20,000 cells/well, IMDM 5% FBS medium). Cultures were incubated subsequently for 5 days at 35° C. and the viral cytopathic effect and cell viability were scored microscopically. Scores were normalized and percent inhibition calculated.

MERS-CoV and SARS-CoV Antiviral Screening Assays.

Cell-based antiviral screening assays were performed as described previously.(23-24) In brief, Huh7, Vero, and VeroE6 cells were seeded in transparent 96-well plates at a density of $10^4$ (Huh7, VeroE6) or $2\times10^4$ (Vero) cells per well, respectively. After overnight growth, Vero and Huh7 cells were infected with MERS-CoV (strain EMC/2012) and VeroE6 cells were infected with SARS-CoV (strain Frankfurt-1) at an MOI of 0.005. All work with live MERS-CoV and SARS-CoV was performed inside biosafety cabinets in a biosafety level 3 facility at the Leiden University Medical Center. Infected cells were given compound 2 or DMSO (solvent control) prior to infection. For $EC_{50}$ determination, two (for Huh7) or three days (for Vero and VeroE6 cells) after incubation, differences in cell viability caused by virus-induced CPE or by compound-specific side effects were analyzed using the CellTiter 96® $AQ_{ueous}$ Non-Radioactive Cell Proliferation Assay (Promega), according to the manufacturer's instructions. Absorbance ($A_{490}$) was measured using a Berthold Mithras LB 940 96-well plate reader. For $CC_{50}$ determination, cytotoxic effects caused by compound treatment alone were monitored in parallel plates containing mock-infected cells. $EC_{50}$ and $CC_{50}$ values were calculated with GraphPad Prism 5 software using the nonlinear regression model using the results of two independent experiments.

REFERENCES

The contents of the following references are hereby incorporated by reference herein for all purposes.

1. In Global alert and response. Middle East Respiratory syndrome coronavirus (MERS-CoV); World Health Organization: 2015; Vol. 2014.
2. E. L. Tan, E. E. Ooi, C. Y. Lin, H. C. Tan, A. E. Ling, B. Lim, L. W. Stanton, *Emerg. Infect. Dis.,* 10 (2004), p. 581.
3. H. Momattin, K. Mohammed, A. Zumla, Z. A. Memish, J. A. Al-Tawfiq, *Int. J. Infect. Dis.,* 17 (2013), p. e792.
4. J. A. Al-Tawfiq, H. Momattin, J. Dib, Z. A. Memish, *Int. J. Infect. Dis.,* 20 (2014), p. 42.
5. B. Morgenstern, M. Michaelis, P. C. Baer, H. W. Doerr, J. Cinatl Jr., *Biochem. Biophys. Res. Commun.,* 326 (2005), p. 905.
6. F. Chen, K. H. Chan, Y. Jiang, R. Y. Kao, H. T. Lu, K. W. Fan, V. C. Cheng, W. H. Tsui, I. F. Hung, T. S. Lee, Y. Guan, J. S. Peiris, K. Y. Yuen, *J. Clin. Virol.,* 31 (2004), p. 69.
7. D. Falzarano, E. de Wit, A. L. Rasmussen, F. Feldmann, A. Okumura, D. P. Scott, D. Brining, T. Bushmaker, C. Martellaro, L. Baseler, A. G. Benecke, M. G. Katze, V. J. Munster, H. Feldmann, *Nat. Med.,* 19 (2013), p. 1313.
8. E. C. Smith, H. Blanc, M. Vignuzzi, M. R. Denison, *PLoS Pathog.,* 9 (2013), p. e1003565.
9. K. Pyrc, B. Berkhout, L. van der Hoek, *Expert Rev. Anti-infect. Ther.,* 5 (2007), p. 245.
10. J. S. Peiris, S. T. Lai, L. L. Poon, Y. Guan, L. Y. Yam, W. Lim, J. Nicholls, W. K. Yee, W. W. Yan, M. T. Cheung, V. C. Cheng, K. H. Chan, D. N. Tsang, R. W. Yung, T. K. Ng, K. Y. Yuen, *Lancet,* 361 (2003), p. 1319.
11. S. Quirk, K. L. Seley, *Biochemistry,* 44 (2005), p. 10854.
12. K. L. Seley, S. Quirk, S. Salim, L. Zhang, A. Hagos, *Bioorg. Med. Chem. Lett.,* 2003 (1985), p. 13.
13. K. L. Seley, S. Salim, L. Zhang, *Org. Lett.,* 7 (2005), p. 63.
14. K. L. Seley, L. Zhang, A. Hagos, *Org. Lett.,* 3 (2001), p. 3209.
15. K. L. Seley, L. Zhang, A. Hagos, S. Quirk, *J. Org. Chem.,* 67 (2002), p. 3365.
16. O. R. Wauchope, M. Velasquez, K. Seley-Radtke, Synthesis, 44 (2012), p. 3496.
17. S. Quirk, K. L. Seley, *Biochemistry,* 44 (2005), p. 13172.
18. In Zovirax Prescribing Information; U. S. Food and Drug Administration: 2003; NDA 18-603/5-027.
19. C. Vanpouille, A. Lisco, M. Derudas, E. Saba, J. C. Grivel, B. Brichacek, F. Scrimieri, R. Schinazi, D. Schols, C. McGuigan, J. Balzarini, L. Margolis, *J. Infect. Dis.,* 201 (2010), p. 635.
20. Boncel, A. Gondela, M. Maczka, M. Tuszkiewicz-Kuznik, P. Grec, B. Hefczyc, K. Walczak, *Synthesis-Stuttgart* (2011), p. 603.
21. R. Schinazi, *J. Org. Chem.,* 50 (1985), p. 841.
22. S. P. Mee, V. Lee, J. E. Baldwin, *Chemistry,* 11 (2005), p. 3294.
23. A. H. de Wilde, V. S. Raj, D. Oudshoorn, T. M. Bestebroer, S. van Nieuwkoop, R. W. Limpens, C. C. Posthuma, Y. van der Meer, M. Barcena, B. L. Haagmans, E. J. Snijder, B. G. van den Hoogen, *J. Gen. Virol.,* 94 (2013), p. 1749.
24. A. H. de Wilde, D. Jochmans, C. C. Posthuma, J. C. Zevenhoven-Dobbe, S. van Nieuwkoop, T. M. Bestebroer, B. G. van den Hoogen, J. Neyts, E. J. Snijder, *Antimicrob. Agents Chemother.,* 58 (2014), p. 4875.
25. P. A. Furman, *J. Biol. Chem.,* 259 (1984), p. 9575.
26. P. V. McGuirt, P. A. Furman, *Am. J. Med.,* 73 (1982), p. 67.
27. C. McGuigan, K. Madela, M. Aljarah, A. Gilles, A. Brancale, N. Zonta, S. Chamberlain, J. Vernachio, J. Hutchins, A. Hall, B. Ames, E. Gorovits, B. Ganguly, A. Kolykhalov, J. Wang, J. Muhammad, J. M. Patti, G. Henson, *Bioorg. Med. Chem. Lett.,* 20 (2010), p. 4850.
28. Jochmans, D.; Leyssen, P.; Neyts, J. A novel method for high-throughput screening to quantify antiviral activity against viruses that induce limited CPE. *J Virol Methods* 2012, 183, 176-9.
29. Fouchier, R. A.; Hartwig, N. G; Bestebroer, T. M.; Niemeyer, B.; de Jong, J. C.; Simon, J. H.; Osterhaus, A. D. A previously undescribed coronavirus associated with respiratory disease in humans. *Proc Natl Acad Sci USA* 2004, 101, 6212-6.
30. Kuiken, T.; van den Hoogen, B. G; van Riel, D. A.; Laman, J. D.; van Amerongen, G; Sprong, L.; Fouchier, R. A.; Osterhaus, A. D. Experimental human metapneumovirus infection of cynomolgus macaques (*Macaca fascicularis*) results in virus replication in ciliated epithelial cells and pneumocytes with associated lesions throughout the respiratory tract. *Am J Pathol* 2004, 164, 1893-900.

That which is claimed is:

1. An acyclic fleximer nucleoside analogue having antiviral activity selected from the following compounds:

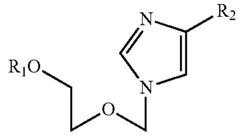

Wherein $R_1$ is H or $CH_3(C{=}O)$ and $R_2$ is selected from the group consisting of d, e and f

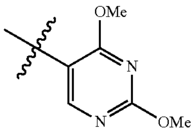

d

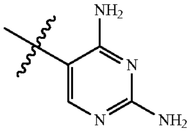

e and

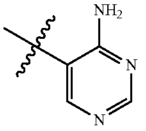

f or a pharmaceutically acceptable salt, hydrate, prodrug or solvate thereof.

2. A acyclic fleximer nucleoside having the following structure:

19

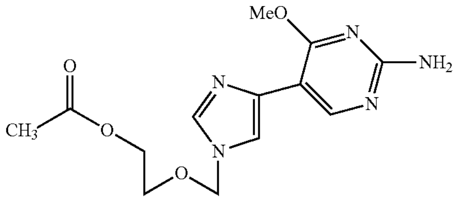

or a pharmaceutically acceptable salt, isomer, hydrate, prodrug or solvate thereof.

3. A composition comprising the acyclic fleximer nucleoside analogue according to claim 1 and a pharmaceutically acceptable carrier.

4. The composition according to claim 3, further comprising an additional antiviral agent.

5. A composition comprising the acyclic fleximer nucleoside analogue according to claim 2, and a pharmaceutically acceptable carrier.

6. The composition according to claim 5, further comprising an additional antiviral agent.

7. A method of treating and/or reducing the effects of a coronavirus in a subject in need of such treatment, the method comprising administering a therapeutically effective amount of an acyclic fleximer nucleoside analogue selected from the group consisting of:

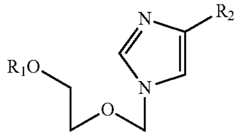

Wherein $R_1$ is H or $CH_3(C{=}O)$ and $R_2$ is selected from the group consisting of d, e and f

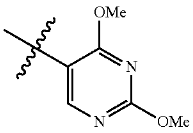

d

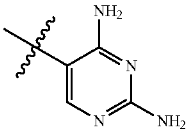

e and

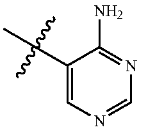

f or a pharmaceutically acceptable salt, isomer, hydrate, prodrug or solvate thereof.

8. A method of treating and/or reducing the effects of a coronavirus in a subject in need of such treatment, the method comprising administering a therapeutically effective amount of an acyclic fleximer nucleoside analogue having the following structure:

19

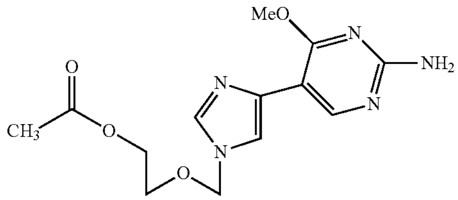

or a pharmaceutically acceptable salthydrate, prodrug or solvate thereof.

9. The method of claim 8, wherein the acyclic fleximer nucleoside analogue is structure 19 and the coronavirus is severe acute respiratory syndrome (SARS) or Middle East respiratory syndrome (MERS).

10. The method of claim 8, wherein the acyclic fleximer nucleoside analogue is in a composition further comprising a pharmaceutically acceptable carrier.

11. The method of claim 8, wherein the acyclic fleximer nucleoside analogue is in a composition further comprising an additional antiviral agent.

12. The method of claim 8, wherein the therapeutically effective amount of the acyclic fleximer nucleoside analogue is from 0.05 to 50 mg per kilogram body weight of the subject per day.

* * * * *

UNITED STATES PATENT AND TRADEMARK OFFICE
CERTIFICATE OF CORRECTION

PATENT NO. : 10,226,434 B2  
APPLICATION NO. : 16/025284  
DATED : March 12, 2019  
INVENTOR(S) : Katherine L. Radtke et al.

Page 1 of 1

It is certified that error appears in the above-identified patent and that said Letters Patent is hereby corrected as shown below:

On the Title Page

Assignees: University of Maryland, Baltimore County, Baltimore, MD (US); Katholieke Universiteit Leuven/Leiden University Medical Center, RC Leiden, Belgium (NL)

Should be:
Assignees: University of Maryland, Baltimore County, Baltimore, MD (US); Katholieke Universiteit Leuven (BE); Leiden University Medical Center, RC Leiden (NL)

Signed and Sealed this  
Thirtieth Day of April, 2019

Andrei Iancu  
*Director of the United States Patent and Trademark Office*